(12) United States Patent
Cao et al.

(10) Patent No.: US 11,701,051 B2
(45) Date of Patent: Jul. 18, 2023

(54) METHOD AND SYSTEM FOR DETECTING ARRHYTHMIAS IN CARDIAC ACTIVITY

(71) Applicant: Pacesetter, Inc., Sylmar, CA (US)

(72) Inventors: Diming Cao, Valley Village, CA (US); Fady Dawoud, Studio City, CA (US)

(73) Assignee: Pacesetter, Inc., Sylmar, CA (US)

( * ) Notice: Subject to any disclaimer, the term of this patent is extended or adjusted under 35 U.S.C. 154(b) by 270 days.

(21) Appl. No.: 17/167,149

(22) Filed: Feb. 4, 2021

(65) Prior Publication Data

US 2021/0290140 A1 Sep. 23, 2021

Related U.S. Application Data

(60) Provisional application No. 62/991,101, filed on Mar. 18, 2020.

(51) Int. Cl.

| | |
|---|---|
| *A61B 5/00* | (2006.01) |
| *A61B 5/35* | (2021.01) |
| *A61B 5/353* | (2021.01) |
| *A61B 5/352* | (2021.01) |
| *G16H 50/30* | (2018.01) |
| *A61B 5/355* | (2021.01) |
| *A61B 5/363* | (2021.01) |
| *A61B 5/361* | (2021.01) |

(52) U.S. Cl.
CPC .............. *A61B 5/35* (2021.01); *A61B 5/352* (2021.01); *A61B 5/353* (2021.01); *A61B 5/355* (2021.01); *G16H 50/30* (2018.01); *A61B 5/361* (2021.01); *A61B 5/363* (2021.01)

(58) Field of Classification Search
CPC ........... A61B 5/35; A61B 5/352; A61B 5/353; A61B 5/355; A61B 5/361; A61B 5/363; G16H 50/30
See application file for complete search history.

(56) References Cited

U.S. PATENT DOCUMENTS

| | | | |
|---|---|---|---|
| 5,313,953 A | * | 5/1994 | Yomtov ............... A61N 1/3702 600/517 |
| 3,000,790 A1 | | 8/2011 | Bjorling et al. |
| 2011/0125206 A1 | | 5/2011 | Bornzin et al. |
| 2013/0138006 A1 | | 5/2013 | Bornzin et al. |

* cited by examiner

*Primary Examiner* — Scott M. Getzow
(74) *Attorney, Agent, or Firm* — The Small Patent Law Group LLC; Dean D. Small

(57) ABSTRACT

Systems and methods for detecting arrhythmias in cardiac activity are provided and include memory to store specific executable instructions. One or more processors are configured to execute the specific executable instructions for obtaining first and second far field cardiac activity (CA) data sets over primary and secondary sensing channels, respectively, in connection with a series of beats. The system detects candidate atrial features from the second CA data set, identifies ventricular features from the first CA data set and utilizes the ventricular features to separate beat segments within the second CA data set. The system automatically iteratively analyzes the beat segments by overlaying an atrial activity search window with the second CA data set and determines whether one or more of the candidate atrial features occur within the atrial activity search window. The system adjusts an atrial sensitivity profile based on whether the atrial activity search window includes the one or more of the candidate atrial features and detects atrial events based on the atrial sensitivity profile.

20 Claims, 10 Drawing Sheets

METHOD AND SYSTEM FOR DETECTING ARRHYTHMIAS IN CARDIAC ACTIVITY

REFERENCE TO RELATED APPLICATIONS

The present application claims priority to U.S. Provisional Application No. 62/991,101, Titled "METHOD AND SYSTEM FOR DETECTING ARRYTHMIAS IN CARDIAC ACTIVITY" which was filed on 18 Mar. 2020, the complete subject matter of which is expressly incorporated herein by reference in its entirety. FIELD OF THE INVENTION

FIELD OF THE INVENTION

Embodiments herein relate generally to implantable medical devices, and more particularly to detecting arrythmias in cardiac activity.

BACKGROUND OF THE INVENTION

Cardiac monitoring systems have been developed for use in an ambulatory setting, which may be either external, such as a Holter monitor, or internal, such as implantable cardiac monitors (ICMs) or "loop recorders". These systems continually sense cardiac electrical signals from a patient's heart, process the signals to detect arrhythmias, and upon detection, record the electrical signals for subsequent review and analysis.

More recently, interest has increased in providing improved ICMs. It has been proposed that ICMs may be used for collecting electrocardiogram (ECG) signals and diagnosing various arrhythmias, including tachycardia, Bradycardia, asystole, and the like. Under-sensing is a widespread challenge inherent in sensing ECG signals by remote cardiac measurements (non-vascular, e.g., subcutaneous or substernal) due to loss of device-skin contact, posture change or other means. Even though clinical programming during implantation tries to optimize sensing parameters, ECG R-wave amplitudes change over time (e.g., mostly decrease over time) leading to false triggers due to under-sensing of the ECG signal.

An approach, that is employed in ICMs to mitigate under-sensing, is to use a secondary confirmation algorithm. The secondary confirmation algorithm uses a measured or filtered ECG signal after a tachycardia, Bradycardia, or asystole episode is declared. FIG. 1A illustrates a current flow of ICM primary detection and secondary confirmation processing. When a primary detection process determines that all criteria are satisfied for Bradycardia, tachycardia, or an asystole arrhythmia, a secondary confirmation process is initiated.

FIG. 1B illustrates a conventional ECG strip and episode marker. As shown in FIG. 1B, once the primary detection process completes the analysis and declares a potential episode, a period of time (e.g., 1 second) passes before the secondary confirmation process completes analysis. The secondary confirmation process uses a more sensitive threshold to further verify the presence of arrhythmic beats. The ICM holds the outcome of the primary detection process as a potential episode until the secondary confirmation process analyzes a segment of ECG data. The ICM does not label the potential episode with an episode marker (e.g., "Brady" or the like) until the secondary confirmation process confirms the episode.

Hence, a noticeable processing delay occurs from the completion of the primary detection process, while the secondary confirmation process analyzes the ECG data, until the secondary confirmation generates an outcome confirming or rejecting the candidate episode. An ECG strip and marker are displayed. However, the delay introduces a visible offset on the display between a location where an episode marker is inserted onto an ECG signal and the actual point along the ECG signal where the arrhythmia episode occurred. In the example of FIG. 1B, the actual Brady episode should be labeled with a marker at the 10 second "10 s" time point along the ECG strip, but instead the "Brady" marker is inserted after the 11th second "11 s" along the ECG strip. The Bradycardia marker is positioned along the ECG strip over 1 second after the actual point at which the Bradycardia episode was declared.

Further, the secondary confirmation algorithm uses logic operations to either confirm or reject a potential episode in addition to the primary detection operation. After the primary detection process declares a potential episode, the secondary confirmation logic then begins to process the available data, before the ICM generates and records an episode marker with the ECG signals. Depending on the ICM setting, the secondary confirmation process can delay generation (e.g., by 0.3 or more seconds) of the episode marker on a display of a programmer or on a patient care network report. The time needed for the secondary confirmation algorithm to confirm or deny an episode can also inhibit or delay execution of discriminators leading to user confusion.

Also, a common reason for declaration of false episodes is that the primary detection process experiences persistent under-sensing for an extended duration of time. Persistent under-sensing causes the ICM to utilize undue processor power to appropriately handle the under-sensed events (both by primary detection and secondary confirmation processes) which can translate to shortened device longevity from days to months. Further, under-sensing can lead to undue use of storage space to store inappropriate arrhythmia episodes as well as excessive communications sessions to transmit stored episodes to an external instrument.

An opportunity remains to accelerate the process for confirming or rejecting arrhythmia episodes as well as to better align in time recorded and displayed episode markers and cardiac activity signals on a display and report.

SUMMARY

In accordance with embodiments herein, a system for detecting arrhythmias in cardiac activity is provided. The system includes memory to store specific executable instructions. One or more processors are configured to execute the specific executable instructions for obtaining first and second far field cardiac activity (CA) data sets over primary and secondary sensing channels, respectively, in connection with a series of beats. The system detects candidate atrial features from the second CA data set, identifies ventricular features from the first CA data set and utilizes the ventricular features to separate beat segments within the second CA data set. The system automatically iteratively analyzes the beat segments by overlaying an atrial activity search window with the second CA data set and determines whether one or more of the candidate atrial features occur within the atrial activity search window. The system adjusts an atrial sensitivity profile based on whether the atrial activity search window includes the one or more of the candidate atrial features and detects atrial events based on the atrial sensitivity profile.

Optionally, the primary and secondary sensing channels may correspond to ventricular and atrial sensing channels respectively. the one or more processors may be configured to identify peaks in the second CA data set as the candidate atrial features. The one or more processors may be configured to identify the ventricular features by identifying R-waves in the first CA data set. The adjusting may further comprise reducing a sensitivity level of the sensitivity profile when the determining determines that the atrial activity search window does not include the one or more candidate atrial features. The adjusting may further comprise raising a sensitivity level of the sensitivity profile when the determining determines that the atrial activity search window does include the one or more candidate atrial features.

Optionally, the candidate atrial features may include detecting candidate P-wave features and saving the candidate P-wave features to a candidate P-wave list. The determining operation may include determining whether one or more of the candidate P-wave features occur within the atrial activity search window. The candidate atrial features may correspond to P-wave peaks. The automatically iteratively analyzing the beat segments may maintain an estimate of a P-wave peak amplitude. Ventricular features may correspond to R-wave peaks. The automatically iteratively analyzing the beat segments may maintain an estimate of a combination of an R-wave peak amplitude and the P-wave peak amplitude.

Optionally, the candidate atrial features may correspond to T-wave peaks. The automatically iteratively analyzing the beat segments may maintain an estimate of a T-wave peak amplitude. Ventricular features may correspond to R-wave peaks. The automatically iteratively analyzing the beat segments may maintain an estimate of a combination of an R-wave peak amplitude and the T-wave peak amplitude. The system may adjust a ventricular sensitivity profile based at least in part on the atrial sensitivity profile.

In accordance with embodiments herein, a method for detecting arrhythmias in cardiac activity is provided. The method is under control of one or more processors configured with specific executable instructions. The method obtains first and second far field cardiac activity (CA) data sets over primary and secondary sensing channels, respectively, in connection with a series of beats. The method detects candidate atrial features from the second CA data set, identifies ventricular features from the first CA data set and utilizes the ventricular features to separate beat segments within the second CA data set. The method automatically iteratively analyze the beat segments by overlaying an atrial activity search window with the second CA data set and determining whether one or more of the candidate atrial features occur within the atrial activity search window. The method adjusts an atrial sensitivity profile based on whether the atrial activity search window includes the one or more of the candidate atrial features and detects atrial events based on the atrial sensitivity profile.

Optionally, the primary and secondary sensing channels may correspond to ventricular and atrial sensing channels respectively. The method may include, as part of detecting candidate atrial features, identifying peaks in the second CA data set as the candidate atrial features. The method may include, as part of identifying ventricular features, identifying R-waves in the first CA data set. The method may further comprise, as part of the adjusting, reducing a sensitivity level of the sensitivity profile when the determining determines that the atrial activity search window does not include the one or more candidate atrial features. The method may further comprise, as part of the adjusting, raising a sensitivity level of the sensitivity profile when the determining determines that the atrial activity search window does include the one or more candidate atrial features.

Optionally, the method may further comprise saving the candidate atrial features to a candidate atrial feature list, and, as part of the determining, determining whether one or more of the candidate atrial features occur within the atrial activity search window. The candidate atrial features may correspond to P-wave peaks. The method may include, as part of the automatically iteratively analyzing the beat segments, maintaining an estimate of a P-wave peak amplitude. Ventricular features may correspond to R-wave peaks. The method may include, as part of the automatically iteratively analyzing the beat segments, maintaining an estimate of a combination of an R-wave peak amplitude and the P-wave peak amplitude.

Optionally, the candidate atrial features may correspond to T-wave peaks. The method may include, as part of the automatically iteratively analyzing the beat segments, maintaining an estimate of a T-wave peak amplitude. Ventricular features may correspond to R-wave peaks. The method may include, as part of the automatically iteratively analyzing the beat segments, maintaining an estimate of a combination of an R-wave peak amplitude and the T-wave peak amplitude. The method may adjust a ventricular sensitivity profile based at least in part on the atrial sensitivity profile.

DETAILED DESCRIPTION

Terms and Abbreviations

Figure 1A:
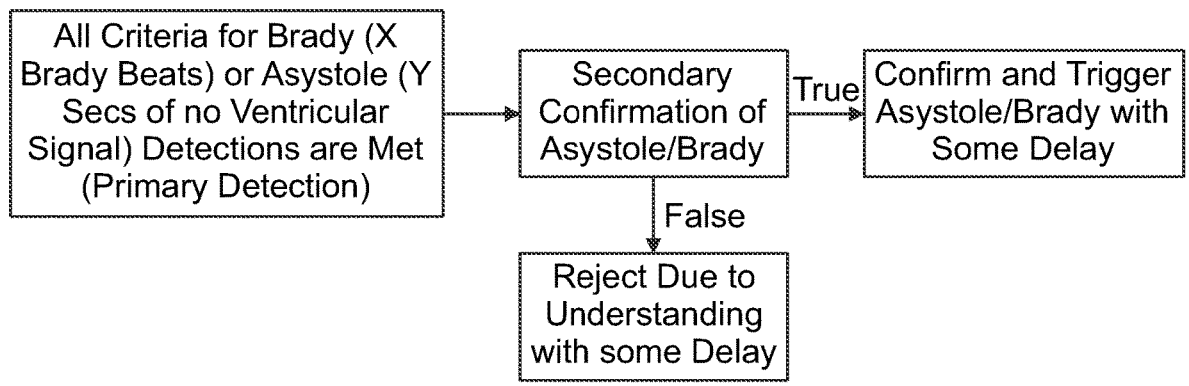
FIG. 1A illustrates a conventional flow of ICM primary detection and secondary confirmation processing.
Figure 1B:
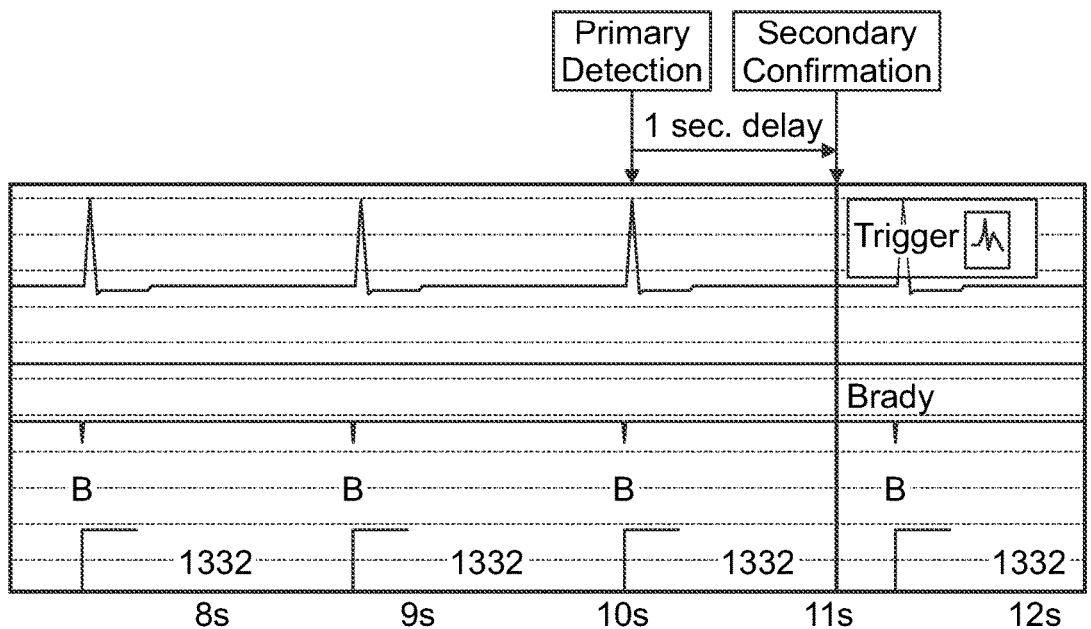
FIG. 1B illustrates a conventional ECG strip and episode marker.

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes.

The terms "cardiac activity data set" and "CA data set" (collectively "CA data set") are used interchangeably to refer to a data set that includes measured CA signals for a series of cardiac events in combination with device documented markers.

The term "marker" refers to data and/or information identified from CA signals that may be presented as graphical and/or numeric indicia indicative of one or more features within the CA signals and/or indicative of one or more episodes exhibited by the cardiac events. Markers may be superimposed upon CA signals or presented proximate to, and temporally aligned with, CA signals. Non-limiting examples of markers may include R-wave markers, noise markers, activity markers, interval markers, refractory markers, P-wave markers, T-wave markers, PVC markers, sinus rhythm markers, AF markers and other arrhythmia markers. As a further non-limiting example, basic event markers may include "AF entry" to indicate a beginning of an AF event, "in AF" to indicate that AF is ongoing, "AF exit" to indicate that AF has terminated, "T" to indicate a tachycardia beat, "B" to indicate a Bradycardia beat, "A" to indicate an asystole beat, "VS" to indicate a regular sinus beat, "Tachy" to indicate a tachycardia episode, "Brady" to indicate a Bradycardia episode, "Asystole" to indicate an asystole episode, "Patient activated" to indicate a patient activated episode. An activity marker may indicate activity detected by activity sensor during the CA signal. Noise markers may indicate entry/start, ongoing, recovery and exit/stop of noise. Markers may be presented as symbols, dashed lines, numeric values, thickened portions of a waveform, and the like. Markers may represent events, intervals, refractory periods, ICM activity, and other algorithm related activity. For example, interval markers, such as the R-R interval, may include a numeric value indicating the duration of the interval. The AF markers indicate atrial fibrillation rhythmic.

The term "COI" refers to a characteristic of interest within CA signals. Non-limiting examples of features of interest include an R-wave, P-wave, T-wave and isoelectric segments. A feature of interest may correspond to a peak of an individual R-wave, an average or median P, R or T-wave peak and the like.

The terms "beat" and "cardiac event" are used interchangeably and refer to both normal and abnormal events.

The terms "normal" and "sinus" are used to refer to events, features, and characteristics of, or appropriate to, a heart's healthy or normal functioning.

The terms "abnormal," or "arrhythmic" are used to refer to events, features, and characteristics of, or appropriate to, an un-healthy or abnormal functioning of the heart.

The term "real-time" refers to a time frame contemporaneous with a normal or abnormal episode occurrence. For example, a real-time process or operation would occur during or immediately after (e.g., within minutes or seconds after) a cardiac event, a series of cardiac events, an arrhythmia episode, and the like.

The terms "sensitivity" and "sensitivity level", as used herein, refer to a threshold that an input CA signal must exceed for an implantable device to identify a CA signal feature of interest (e.g., a P-wave, T-wave, etc.). Increasing the sensitivity includes lowering the threshold that an input CA signal must exceed for an implantable device to identify a CA signal feature of interest. Conversely, decreasing the sensitivity includes raising the threshold that an input CA signal must exceed for an implantable device to identify a CA signal feature of interest. As one non-limiting example, software may be implemented using a programmed sensitivity level to declare a P-wave to be detected when the input CA signal exceeds the current programmed sensitivity level. In response, the software declares a device documented feature (e.g., a P-wave, a T-wave, etc.) marker. The sensitivity level may be defined in various manners based on the nature of the CA signals. For example, when the CA signals measure electrical activity in terms of millivolts, the sensitivity level represents a millivolt threshold. For example, when a cardiac beat with a 0.14 mV amplitude is sensed by a device hardware, a P-wave may be detected when the current sensitivity level is programmed to 0.1 mV. However, when the sensitivity level is programmed to 0.15 mV or above, a cardiac beat with amplitude of 0.14 mV will not be detected as a P-wave. Embodiments herein determine an adaptive sensitivity limit and sensitivity profile for the sensitivity level.

The term "subcutaneous" shall mean below the skin surface, but not transvenous, namely not within a chamber of the heart and not within a vessel on the heart.

Overview

Embodiments herein describe novel methods and systems to significantly reduce the execution time of secondary discriminators by monitoring atrial sense signals (e.g., P-wave amplitude prior to R-wave) prior to any arrythmia triggering. In current systems and methods, the under-sensing discriminators process large amounts of pre-trigger signals in the VIEGM channel before determining the secondary sensing threshold to search for under-sensed signals. Embodiments herein utilize the primary sensing threshold on a primary hardware-based sensing channel to estimate the median peak of the recent ventricular sense signals (e.g., R-wave peak median) and an additional hardware-based sensing channel to track the peak of atrial sense signals (e.g., P-waves) to estimate the P-wave peak median. The secondary sensing threshold employed by secondary discriminators may be derived based on the P-wave peak median and/or the R-wave peak median. The secondary sensing threshold can be used in the secondary discrimination stage to capture under-sensed signals as well as circumvent oversensing of noise or atrial signals. Shifting the P-wave searching function from post-trigger analysis to real-time atrial monitoring leads to significant reduction of battery usage of secondary discrimination (e.g., 90% reduction over current systems) as well as faster execution time (e.g., 95% faster compared to current systems). Additionally or alternatively, embodiments herein can be used to dynamically adjust the primary sensing threshold on every ventricular sense detection to optimize the balance between capturing under-sensing signals while preventing oversensing of noise and/or atrial sensing signals. By dynamically adjusting the primary sensing threshold based on the atrial signal moving median, battery longevity of the ICM may be improved and a significant number of under-sensing or loss of contact events avoided, leading to more predictable ICM longevity. Additionally or alternatively, embodiments herein can be used by an IMD (e.g., a single-chamber ventricular pacemaker and/or ICD) to detect atrial activity on a far field channel to, for example, synchronize ventricular pacing with sinus activation and/or to determine the presence of atrial fibrillation.

Embodiments herein describe novel methods and systems for detecting arrhythmias (e.g., Brady and asystole) in cardiac activity over multiple, real-time sensing channels. To do so, embodiments herein simultaneously collect CA data about ventricular and atrial activity on a beat-by-beat basis over, respectively, a dedicated primary sensing channel and a dedicated secondary sensing channel. The primary sensing channel includes a primary sensitivity profile (e.g., a ventricular sensitivity profile) to facilitate identifying ventricular features of interest (e.g., R-waves), while the secondary sensing channel includes a secondary sensitivity profile (e.g., an atrial sensitivity profile) to facilitate detecting candidate atrial features of interest (e.g., P-waves, T-waves). Ventricular features identified in a first CA data set obtained over the primary sensing channel are used to discriminate the beat segments within a second CA data set over the secondary sensing channel. The beat segments of the second CA data set are automatically iteratively analyzed to determine whether one or more of the candidate atrial features occurred within an atrial activity search window. The atrial sensitivity profile (or threshold) is iteratively analyzed and adjusted based on whether the atrial activity search window includes at least one of the candidate atrial features and atrial events are detected based on the atrial sensitivity profile. Embodiments herein provide for a floating, dynamically adjusting atrial sensitivity profile that avoids under-sensing atrial features of interest and oversensing other atrial features or noise.

Further, when partial conditions of an arrythmia are met within a primary detection process over the primary sensing channel, a secondary confirmation process has CA data indicative of atrial features readily available to expedite processing time of arrythmia confirmation (e.g., via Brady discriminators, asystole discriminators, tachycardia discriminators, PVC discriminators, etc.). The secondary sensing channel is configured to monitor atrial features of interest and determine the amplitude of atrial sensing signals present in the second CA data set. The secondary confirmation process is initiated before an arrhythmia is declared by the primary detection process, such that the secondary confirmation process generates an outcome before or at a common time as completion of the primary detection process. By performing the primary detection and secondary confirmation processes in parallel, methods and systems herein generate and position episode markers at a same point in time along a CA signal/strip (e.g., ECG signals) as an actual point along the CA signal where the arrhythmia was identified. By performing the primary detection and secondary confirmation processes in parallel, methods and systems herein are able to store the episode markers and CA signals in the data storage and/or display the markers and ECG signals with minimal offset or time delay therebetween.

Optionally, the methods and systems herein adjust the primary sensitivity profile utilized with the primary detection process in order to improve ICM longevity by avoiding undue battery drain that would otherwise occur with persistent under-sensing or loss of contact events. To do so, a moving median of atrial sensing signal amplitudes is obtained from the second CA data set and utilized to dynamically adjust the primary sensitivity profile (e.g., the ventricular sensitivity profile). Dynamically adjusting the primary sensitivity profile (or threshold) avoids under-sensing ventricular features of interest while preventing oversensing of noise or atrial sensing signals. Embodiments herein provide for a floating, dynamically adjusting primary sensing profile that improves the longevity of and the predictability of the longevity of the battery of the ICM by reducing battery usage associated with secondary discriminators computational processing.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. Additionally or alternatively, the ICM may include one or more structural and/or functional aspects of the device(s) described in one or more of U.S. patent application Ser. No. 15/973,126, titled "METHOD AND SYSTEM FOR SECOND PASS CONFIRMATION OF DETECTED CARDIAC ARRHYTHMIC PATTERNS"; U.S. patent application Ser. No. 15/973,351, titled "METHOD AND SYSTEM TO DETECT R-WAVES IN CARDIAC ARRHYTHMIC PATTERNS"; U.S. patent application Ser. No. 15/973,307, titled "METHOD AND SYSTEM TO DETECT POST VENTRICULAR CONTRACTIONS IN CARDIAC ARRHYTHMIC PATTERNS"; and U.S. patent application Ser. No. 16/399,813, titled "METHOD AND SYSTEM TO DETECT NOISE IN CARDIAC ARRHYTHMIC PATTERNS", each of which are incorporated herein by reference in their respective entireties.

Additionally or alternatively, the IMD may be a leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

Additionally or alternatively, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. Application Ser. No.: 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

Additionally or alternatively, the IMD may be a leadless cardiac monitor (ICM) that includes one or more structural and/or functional aspects of the device(s) described in U.S. Patent Application, U.S. patent application Ser. No. 15/084, 373, filed Mar. 29, 2016, entitled, "METHOD AND SYSTEM TO DISCRIMINATE RHYTHM PATTERNS IN CARDIAC ACTIVITY," which is expressly incorporated herein by reference.

Embodiments may be implemented in connection with one or more PIMDs. Non-limiting examples of PIMDs may include passive wireless sensors used by themselves or incorporated into or used in conjunction with other implantable medical devices (IMDs) such as cardiac monitoring devices, pacemakers, cardioverters, cardiac rhythm management devices, defibrillators, neurostimulators, leadless monitoring devices, leadless pacemakers, replacement valves, shunts, grafts, drug elution devices, blood glucose monitoring systems, orthopedic implants, and the like. For example, the PIMD may include one or more structural and/or functional aspects of the device(s) described in U.S. Pat. No. 9,265,428 entitled "Implantable Wireless Sensor", U.S. Pat. No. 8,278,941 entitled "Strain Monitoring System and Apparatus", U.S. Pat. No. 8,026,729 entitled "System and Apparatus for In-Vivo Assessment of Relative Position of an Implant", U.S. Pat. No. 8,870,787 entitled "Ventricular Shunt System and Method", and U.S. Pat. No. 9,653,926 entitled "Physical Property Sensor with Active Electronic Circuit and Wireless Power and Data Transmission", which are all hereby incorporated by reference in their respective entireties.

All references, including publications, patent applications and patents, cited herein are hereby incorporated by reference to the same extent as if each reference were individually and specifically indicated to be incorporated by reference and were set forth in its entirety herein.

Figure 2:
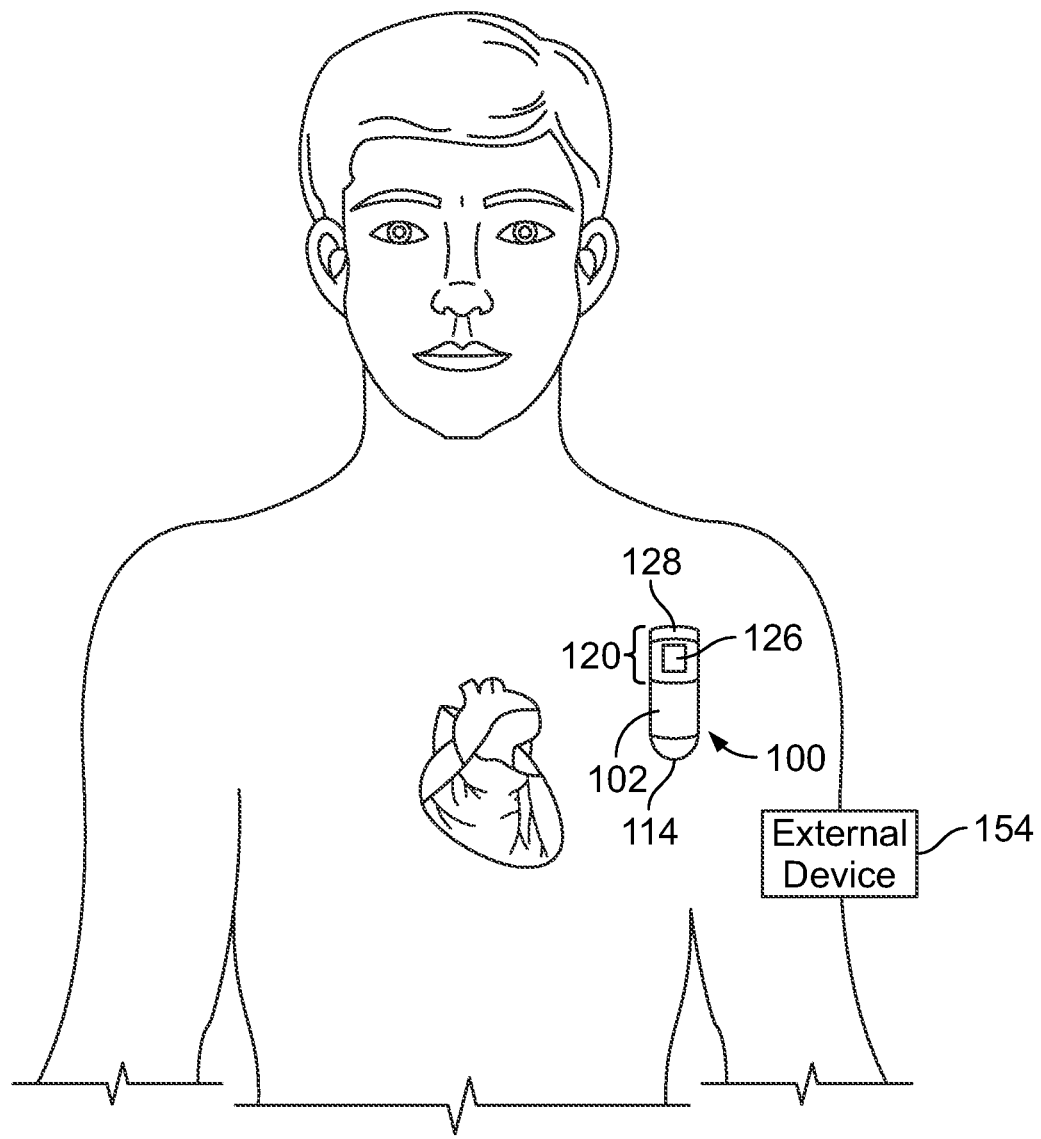
FIG. 2 illustrates an implantable cardiac monitor (ICM) intended for subcutaneous implantation at a site near the heart in accordance with embodiments herein.

FIG. 2 illustrates an implantable cardiac monitoring device (ICM) 100 intended for subcutaneous implantation at a site near the heart. The ICM 100 includes a pair of spaced-apart sense electrodes 114, 126 positioned with respect to a housing 102. The sense electrodes 114, 126 provide for detection of far field ECG signals. Numerous configurations of electrode arrangements are possible. For example, the electrode 114 may be located on a distal end of the ICM 100, while the electrode 126 is located on a proximal side of the ICM 100. Additionally or alternatively, electrodes 126 may be located on opposite sides of the ICM 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 102 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.). The housing 102 includes various other components such as: sense electronics for receiving signals from the electrodes, a microprocessor for processing the signals in accordance with algorithms, such as the arrythmia detection algorithm described herein, a loop memory for temporary storage of CA data, a device memory for long-term storage of CA data upon certain triggering events, such as arrythmia detection, sensors for detecting patient activity and a battery for powering components.

In at least some embodiments, the ICM 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor-tissue interface. The ICM 100 may be configured to be activated by the patient or automatically activated, in connection with recording subcutaneous ECG signals.

The ICM 100 senses far field, subcutaneous CA signals, processes the CA signals to detect arrhythmias and, if an arrhythmia is detected, automatically records the CA signals in memory for subsequent transmission to an external device 154. The CA signal processing and arrythmia detection is provided for, at least in part, by algorithms embodied in or implemented by the microprocessor. The ICM 100 includes one or more processors and memory that stores program instructions directing the processors to implement arrythmia detection and confirmation utilizing an on-board arrythmia discrimination (OAD) process that analyzes cardiac activity signals collected over two or more sensing channels.

Figure 3A:
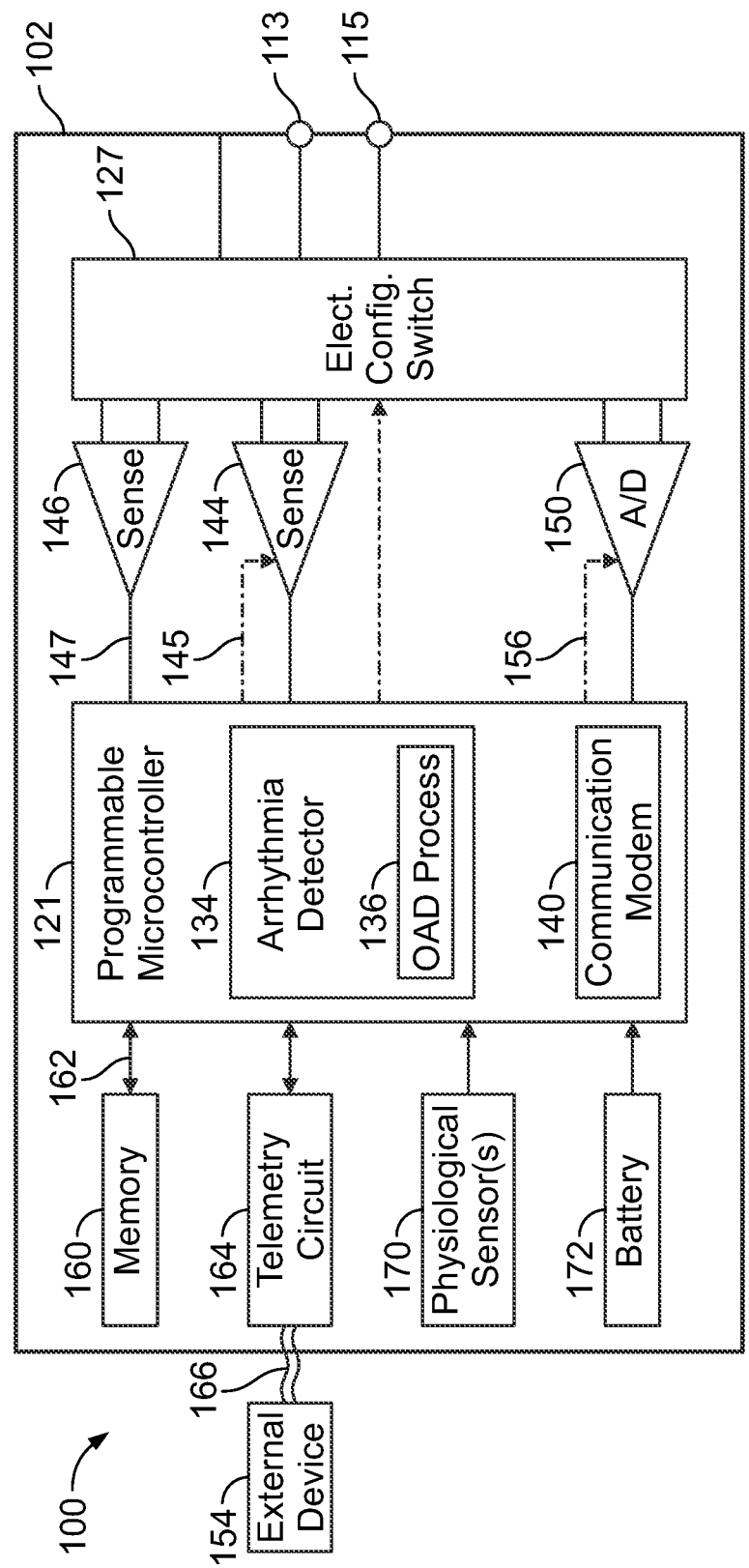
FIG. 3A shows a block diagram of the ICM formed in accordance with embodiments herein.

FIG. 3A shows a block diagram of the ICM 100 formed in accordance with embodiments herein. The ICM 100 may be implemented to monitor both ventricular and atrial activity through sensing circuitry. The ICM 100 has a housing 102 to hold the electronic/computing components. The housing 102 (which is often referred to as the "can", "case", "encasing", or "case electrode") may be programmably selected to act as an electrode for certain sensing modes. Housing 102 further includes a connector (not shown) with at least one terminal 113 and optionally additional terminals 115. The terminals 113, 115 may be coupled to sensing electrodes that are provided upon or immediately adjacent the housing 102. Optionally, more than two terminals 113, 115 may be provided in order to support more than two sensing electrodes, such as for a bipolar sensing scheme that uses the housing 102 as a reference electrode. Additionally or alternatively, the terminals 113, 115 may be connected to one or more leads having one or more electrodes provided thereon, where the electrodes are located in various locations about the heart. The type and location of each electrode may vary.

The ICM 100 includes a programmable microcontroller 121 that controls various operations of the ICM 100, including cardiac monitoring. Microcontroller 121 includes a microprocessor (or equivalent control circuitry), RAM and/or ROM memory, logic and timing circuitry, state machine circuitry, and I/O circuitry. The microcontroller 121 also performs the operations described herein in connection with collecting cardiac activity data and analyzing the cardiac activity data.

A switch 127 is optionally provided to allow selection of different electrode configurations under the control of the microcontroller 121. The electrode configuration switch 127 may include multiple switches for connecting the desired electrodes to the appropriate I/O circuits, thereby facilitating electrode programmability. The switch 127 is controlled by a control signal from the microcontroller 121. Optionally, the switch 127 may be omitted and the I/O circuits directly connected to the housing electrode 114 and a second electrode 126. Microcontroller 121 includes an arrhythmia detector 134 that is configured to analyze cardiac activity signals to identify potential arrhythmias (e.g., Tachycardias, Bradycardias, Asystole, etc.). By way of example, the arrhythmia detector 134 may implement an arrythmia detection algorithm as described in U.S. Pat. No. 8,135,456, the complete subject matter of which is incorporated herein by reference. Although not shown, the microcontroller 121 may further include other dedicated circuitry and/or firmware/software components that assist in monitoring various conditions of the patient's heart and managing pacing therapies.

The ICM 100 is further equipped with a communication modem (modulator/demodulator) 140 to enable wireless communication. In one implementation, the communication modem 140 uses high frequency modulation, for example using RF, Bluetooth, or Bluetooth Low Energy telemetry protocols. The signals are transmitted in a high frequency range and will travel through the body tissue in fluids without stimulating the heart or being felt by the patient. The communication modem 140 may be implemented in hardware as part of the microcontroller 121, or as software/firmware instructions programmed into and executed by the microcontroller 121. Alternatively, the modem 140 may reside separately from the microcontroller as a standalone component. The modem 140 facilitates data retrieval from a remote monitoring network. The modem 140 enables timely and accurate data transfer directly from the patient to an electronic device utilized by a physician.

The ICM 100 includes sensing circuitry 144, 146 selectively coupled to one or more electrodes that perform sensing operations, through the switch 127 to detect cardiac activity. The sensing circuitry 144 is associated with a dedicated primary sensing channel, while the sensing circuitry 146 is associated with a dedicated secondary sensing channel. The sensing circuitry 144, 146 may include dedicated sense amplifiers, multiplexed amplifiers, or shared amplifiers. The sensing circuitry 144, 146 may further employ one or more low power, precision amplifiers with programmable gain and/or automatic gain control, bandpass filtering, and threshold detection circuit to selectively sense the features of interest. In one embodiment, switch 127 may be used to determine the sensing polarity of the cardiac signal by selectively closing the appropriate switches. Additionally or alternatively, the primary and secondary sensing (and any additional) channels may be filtered differently to enhance one desired signal characteristic (T-wave, P-wave, R-wave, ST segment, R-wave/P-wave/T-wave duration, etc.) or suppresses undesired signal characteristic (e.g. noise, sharp signal movements, baseline signal drift, etc.). Filtering may be performed continuously in hardware or on-demand in firmware.

The outputs of the sensing circuitry 144, 146 are connected to the microcontroller 121 which, in turn, determines when to store the cardiac activity data of CA signals (digitized by the ND data acquisition system 150) in the memory 160. For example, the microcontroller 121 may only store the cardiac activity data (from the ND data acquisition system 150) in the memory 160 when a potential episode is detected. The sensing circuitry 144, 146 receives a control signal 145 from the microcontroller 121 for purposes of controlling the gain, threshold, polarization charge removal circuitry (not shown), and the timing of any blocking circuitry (not shown) coupled to the inputs of the sensing circuitry 144, 146.

In the example of FIG. 3A, a primary sensing circuit 144 and a secondary sensing circuit 146 are illustrated. In accordance with one or more embodiments herein, the primary and the secondary sensing channels obtain, respectively, first and second far field CA data sets. The primary sensing channel may be configured to facilitate identifying ventricular features of interest (e.g., R-waves) and secondary sensing channels may be configured to facilitate identifying atrial or ventricular features of interest (e.g., P-waves, T-waves). Optionally, the ICM 100 may include additional sensing circuits, similar to sensing circuits 144, 146, where each sensing circuit is coupled to two or more electrodes and controlled by the microcontroller 121 to sense electrical activity detected at the corresponding two or more electrodes. Additional sensing channels corresponding to the additional sensing circuits may be configured to identify facilitate identifying additional features of interest from the far field CA data sets obtained thereby. The sensing circuits 144, 146 may operate in a unipolar sensing configuration or in a bipolar sensing configuration. Optionally, one or more of the sensing circuits 144, 146 may be removed entirely and the microcontroller 121 configured to perform the operations described herein based upon the CA signals from the A/D data acquisition system 150 directly coupled to the electrodes.

The arrhythmia detector 134 of the microcontroller 121 is configured to obtain first and second far field CA data sets over the primary and secondary sensing channels. The arrythmia detector 134 includes an OAD process 136 that is configured to perform a primary detection process to detect and a secondary confirmation process to confirm arrhythmias, such as tachycardia, Bradycardia, asystole and the like. The OAD process 136 may be implemented as firmware, software and/or circuits.

The OAD process 136 detects the arrhythmia episodes using an automatic detection algorithm that monitors for an irregularity of interest in the ventricular rhythms (e.g., X out of Y beats with a certain R-R-interval length X seconds elapsed with no R-wave, etc.) in the first far field CA data set obtained over the primary sensing channel. For example, the OAD process 136 may implement the arrythmia detection methods described in U.S. Pat. No. 8,135,456, the complete subject matter of which is incorporated herein by reference in its entirety. The OAD process 136 identifies R-waves within the CA signals at points where the CA signal crosses the primary sensitivity profile (outside of a refractory period) on the primary sensing circuitry 144. The OAD process 136 tracks R-wave and RR intervals within the CA signal and identifies arrhythmia events within the CA signal based on a presence or absence of R-waves and the RR interval. When a sufficient number (e.g., X cardiac events out of Y cardiac events) of the cardiac events within the CA signal are identified as arrhythmia events, the OAD process 136 declares a candidate arrhythmia episode.

The OAD process 136 detects and records the locations of candidate atrial events (e.g., P-waves, T-waves) in the second far field CA data set obtained over the secondary sensing channel. The OAD process detects candidate atrial features from the second CA data set at points where the CA signal crosses the secondary sensitivity profile (outside of a refractory period) of the secondary sensing circuitry 146 and identifies ventricular features from the first CA data set. The OAD process 136 uses the ventricular features to separate beat segments within the second CA data set. The OAD process 136 automatically iteratively analyzes the beat segments by overlaying an atrial activity search window with the second CA data set and determining whether the one or more candidate atrial features occur within the atrial activity search window. The atrial activity search window is a selected range of time before an R-wave location. For example, the OAD process 136 identifies P-waves within the CA signals of the second CA data set at points where the CA signal crosses the secondary sensitivity profile within the atrial search window and/or outside of a refractory period. The OAD process 136 adjusts the sensitivity level of the secondary sensitivity profile (e.g., atrial sensitivity profile) on the secondary sensing circuitry 146 iteratively, on a beat-by-beat basis, along with every primary sense detection, based on whether the atrial activity search window includes the one or more candidate atrial features. The OAD process 136 reduces the sensitivity level of the atrial sensitivity profile based on determining that the atrial activity search window does not include the one or more candidate atrial features. Conversely, the OAD process 136 increases the sensitivity level of the atrial sensitivity profile based on determining that the atrial activity search window includes the one or more candidate atrial features. Iteratively adjusting the sensitivity level of the secondary (e.g., atrial) sensitivity profile over a series of beat segments causes the secondary sensitivity profile to converge on the median amplitude of the confirmed atrial features (e.g., the one or more candidate atrial features within the atrial search window), thereby avoiding under-sensing and/or oversensing of atrial events. The OAD process 136 detects atrial events based on the atrial sensitivity profile. Based on detecting an arrythmia episode in the primary detection process, the ventricular feature COI (e.g., R-wave amplitudes) and the secondary sensing threshold (e.g., the median amplitude of P-waves) corresponding to the most recent beats is readily available to expedite the processing time of the secondary discriminator (e.g., Brady, asystole, tachycardia, PVC, etc.).

Optionally, the OAD process 136 may manage a primary sensitivity profile (e.g., a ventricular sensing profile) of the sensing circuitry 144 during detection of ventricular features utilizing the secondary sensitivity profile.

The OAD process 136, and other circuits, systems and methods herein, may be implemented in accordance with the embodiments described in pending application Ser. No. 15/973,351, filed May 7, 2018 and titled "Method and System to Detect R-Waves in Cardiac Arrhythmic Patterns", the complete subject matter of which is incorporated herein by reference in its entirety.

Figure 3B:
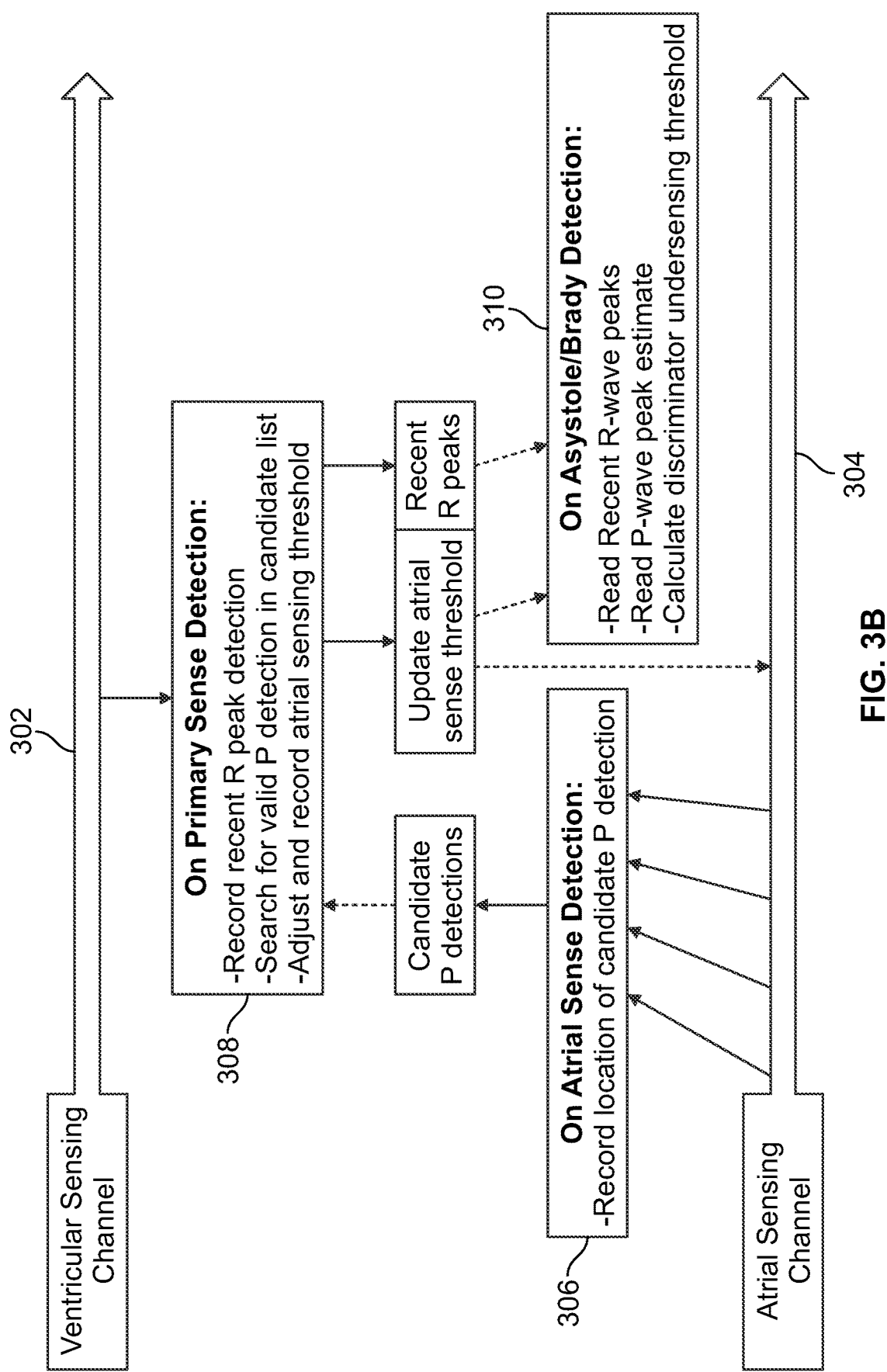
FIG. 3B illustrates the operation of a ventricular sensing process and an atrial sensing process implemented in accordance with embodiments herein.

FIG. 3B illustrates one example of the parallel operation of the primary detection process and the secondary confirmation process in the OAD process 136 accordance with embodiments herein. The primary sensing channel is a ventricular sensing channel 302 and the secondary sensing channel is an atrial sensing channel 304. The OAD process 136 continuously obtains the first far field CA data set over the ventricular sensing channel 302 using a ventricular sensitivity profile in the primary detection process and continuously obtains the second far field CA data set over the atrial sensing channel 304 using an atrial sensitivity profile in the secondary. At 306, the OAD process 136 detects candidate atrial features (e.g., P waves, T-waves, etc.) from the second CA data set at points where the CA signal crosses the atrial sensitivity profile (outside of a refractory period) and records the location of each candidate atrial feature.

At 308, based on detecting a ventricular feature (e.g., an R-wave peak) from the first CA data set at a point where the CA signal crosses the ventricular sensitivity profile, the OAD process 136 records the ventricular feature and searches the list of candidate atrial events for valid atrial events (e.g., P-waves, T-waves). The OAD process 136 uses the ventricular features to separate beat segments within the second CA data set and to define an atrial activity search window (e.g., a P-R interval) preceding the location of the ventricular feature. The OAD process 136 manages the atrial sensing profile of the secondary sensing circuit 146 by adjusting the sensitivity level of the atrial sensing profile over time and on a beat-by-beat basis based on whether the atrial activity search window includes the one or more candidate atrial features. The OAD process 136 either increases or reduces the sensitivity level of the atrial sensitivity profile, respectively, based on determining that the atrial activity search window includes or does not include the one or more candidate atrial features. Iteratively adjusting the sensitivity level of the atrial sensitivity profile over a series of beat segments causes the secondary sensitivity profile to converge on the median amplitude of the confirmed atrial features (e.g., the one or more candidate atrial features within the atrial search window).

At 310, the OAD process 136 utilizes the updated atrial or ventricular sensitivity profile (e.g., the P-wave peak median, the T-wave peak median) to detect atrial events and the recent ventricular features (e.g., R-waves) to calculate the secondary discriminators (e.g., Brady, asystole, tachycardia, PVC, etc.) and confirm arrythmia detection.

The operations described at 306, 308, and 310 are real-time and interrupt-based, so that each of the operations execute based on conditions being met for the respective operation to run.

Optionally, OAD process 136 may manage the ventricular sensing profile of the primary sensing circuit 144 by adjusting the sensitivity level of the ventricular sensing profile based on the atrial sensitivity profile. The sensitivity profile parameters may be adjusted in accordance with embodiments herein, such as to avoid persistent under-sensing or oversensing of ventricular features.

Returning to FIG. 3A, the ICM 100 further includes an analog-to-digital ND data acquisition system (DAS) 150 coupled to one or more electrodes via the switch 127 to sample cardiac activity signals across any pair of desired electrodes. The data acquisition system 150 is configured to acquire ECG signals as CA signals, convert the raw analog data into digital data, and store the digital data as CA data for later processing and/or telemetric transmission to an external device 154 (e.g., a programmer, local transceiver, or a diagnostic system analyzer). The data acquisition system 150 is controlled by a control signal 156 from the microcontroller 121. The EGM signals may be utilized as the cardiac activity data that is analyzed for potential arrhythmia episodes.

By way of example, the external device 154 may represent a bedside monitor installed in a patient's home and utilized to communicate with the ICM 100 while the patient is at home, in bed, or asleep. The external device 154 may be a programmer used in the clinic to interrogate the ICM 100, retrieve data and program detection criteria, and other features. The external device 154 may be a handheld device (e.g., smartphone, tablet device, laptop computer, smartwatch and the like) that can be coupled over a network (e.g., the Internet) to a remote monitoring service, medical network, and the like. The external device 154 facilitates access by physicians to patient data as well as permitting the physician to review real-time CA signals while collected by the ICM 100.

The microcontroller 121 is coupled to a memory 160 by a suitable data/address bus 162. The programmable operating parameters used by the microcontroller 121 are stored in memory 160 and used to customize the operation of the ICM 100 to suit the needs of a particular patient. Such operating parameters define, for example, detection rate thresholds, sensitivity, automatic features, arrythmia detection criteria, activity sensing or other physiological sensors, and electrode polarity, etc.

In addition, the memory 160 stores the cardiac activity data, as well as the markers and other data content associated with detection of arrhythmia episodes. The operating parameters of the ICM 100 may be non-invasively programmed into the memory 160 through a telemetry circuit 164 in telemetric communication via communication link 166 with the external device 154. The telemetry circuit 164 allows ECGs and status information relating to the operation of the ICM 100 (as contained in the microcontroller 121 or memory 160) to be sent to the external device 154 through the established communication link 166. In accordance with embodiments herein, the telemetry circuit 164 conveys the cardiac activity data, markers and other information related to episodes.

The ICM 100 may further include magnet detection circuitry (not shown), coupled to the microcontroller 121, to detect when a magnet is placed over the unit. A magnet may be used by a clinician to perform various test functions of the housing 102 and/or to signal the microcontroller 121 that the external device 154 is in place to receive or transmit data to the microcontroller 121 through the telemetry circuits 164.

The ICM 100 can further include one or more physiologic sensors 170. Such sensors are commonly referred to (in the pacemaker arts) as "rate-responsive" or "exercise" sensors. The physiological sensor 170 may further be used to detect changes in the physiological condition of the heart, or diurnal changes in activity (e.g., detecting sleep and wake states). Signals generated by the physiological sensors 170 are passed to the microcontroller 121 for analysis and optional storage in the memory 160 in connection with the cardiac activity data, markers, episode information and the like. While shown as being included within the housing 102, the physiologic sensor(s) 170 may be external to the housing 102, yet still be implanted within or carried by the patient. Examples of physiologic sensors might include sensors that, for example, activity, temperature, sense respiration rate, pH of blood, ventricular gradient, activity, position/posture, minute ventilation (MV), and so forth.

A battery 172 provides operating power to all of the components in the ICM 100. The battery 172 is capable of operating at low current drains for long periods of time. The battery 172 also desirably has a predictable discharge characteristic so that elective replacement time can be detected. As one example, the housing 102 employs lithium/silver vanadium oxide batteries. The battery 172 may afford various periods of longevity (e.g., three years or more of device monitoring). In alternate embodiments, the battery 172 could be rechargeable. See for example, U.S. Pat. No. 7,294,108, Cardiac event micro-recorder and method for implanting same, which is hereby incorporated by reference.

The ICM 100 provides a simple to configure data storage option to enable physicians to prioritize data based on individual patient conditions, to capture significant events and reduce risk that unexpected events are missed. The ICM 100 may be programmable for pre- and post-trigger event storage. For example, the ICM 100 may be automatically activated to store 10-120 seconds of CA data prior to an event of interest and/or to store 10-120 seconds of post CA data. Optionally, the ICM 100 may afford patient triggered activation in which pre-event CA data is stored, as well as post event CA data (e.g., pre-event storage of 1-15 minutes and post-event storage of 1-15 minutes). Optionally, the ICM 100 may afford manual (patient triggered) or automatic activation for CA data. Optionally, the ICM 100 may afford additional programming options (e.g., asystole duration, Bradycardia rate, tachycardia rate, tachycardia cycle count). The amount of CA data storage may vary based upon the size of the memory 160.

The ICM 100 may provide comprehensive safe diagnostic data reports including a summary of heart rate, in order to assist physicians in diagnosis and treatment of patient conditions. By way of example, reports may include episodic diagnostics for auto trigger events, episode duration, episode count, episode date/time stamp and heart rate histograms. The ICM 100 may be configured to be relatively small (e.g., between 2-10 cc in volume) which may, among other things, reduce risk of infection during implant procedure, afford the use of a small incision, afford the use of a smaller subcutaneous pocket and the like. The small footprint may also reduce implant time and introduce less change in body image for patients.

Figure 4:
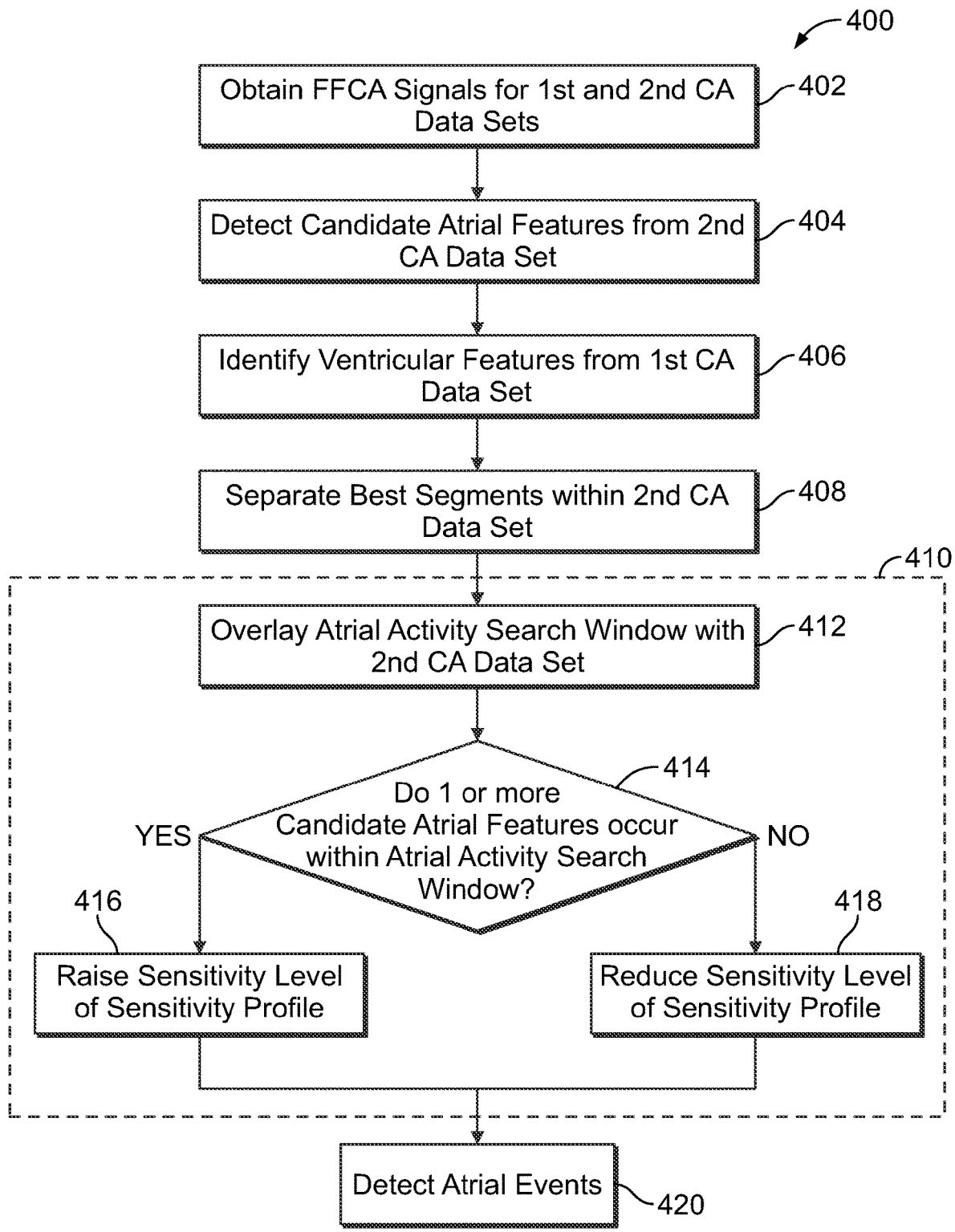
FIG. 4 illustrates a flow chart for a process to detect atrial sensing features in accordance with embodiments herein.

FIG. 4 illustrates a flow chart for a process for detecting atrial sensing features in accordance with embodiments herein. All or a portion of the operations of FIG. 4 may be implemented by one or more processors of the ICM 100 configured with executable instructions. Portions of the operations of FIG. 4 may also be implemented by one or more processors of one or more of a local external device and/or a remote server.

At 402, one or more processors of the ICM obtain a far field cardiac activity (CA) data sets over primary and secondary sensing channels, respectively, in connection with a series of beats. The primary and secondary sensing channels may correspond, respectively, to ventricular and atrial sensing channels. The CA data sets obtained at 502 may be limited to a first CA data set and a second CA data set. Optionally, the CA data sets may also include additional CA data sets corresponding to the primary or secondary sensing channels, or additional sensing channels. For example, the sensing channels may include ventricular or atrial sensing channels. The sensing channels may be the similarly or differently filtered to enhance one or more desired signal characteristic (T-wave, P-wave, R-wave, ST segment, R-wave/P-wave/T-wave duration, etc.) or suppresses one or more undesired signal characteristics (e.g. noise, sharp signal movements, baseline signal drift, etc.). Additionally or alternatively, filtering on one or more sensing channels may be performed continuously in hardware or on-demand in firmware. Although the operations of FIG. 4 are described in at least a partially serial manner, it is recognized that at least a portion of the operations are performed in parallel. For example, far field CA signals may be obtained continuously through the operations of FIG. 4, while primary detection and/or secondary confirmation processes analyze the incoming CA signals. The far field CA signals may be recorded in a circular buffer in a first-in-first-out manner. The buffer may be large enough to retain CA signals for a desired number of seconds and/or beats (e.g., 30-60 seconds and/or 15-30 beats). For example, the buffer may be provided with a size sufficient to retain the first CA data set and the second CA data set.

At 404, the one or more processors detect candidate atrial features from the second CA data set. The process detects candidate atrial features from the second CA data set at points where the CA signal crosses the secondary sensitivity profile (outside of a refractory period) of the secondary sensing circuitry 146. The one or more processors may be configured to identify peaks in the second CA data set as the candidate atrial features. In one or more embodiments, the process may detect, as the candidate atrial features, candidate P-wave features. The candidate P-wave features may correspond to P-wave peaks. The process may save the candidate P-wave features and corresponding locations and/or time stamps to a candidate P-wave list. In additional or alternative embodiments, the candidate atrial features correspond to T-wave features. The candidate T-wave features may correspond to T-wave peaks. The process may save the candidate T-wave features and corresponding locations and/or time stamps to a candidate T-wave list.

At 406, the one or more processors identify ventricular features from the first CA data set. The one or more processors may be configured to identify the ventricular features by identifying R-waves, and the corresponding locations and/or time stamps, in the first CA data set. R-waves are identified within the CA signals at points where the CA signal crosses the primary sensitivity profile (outside of a refractory period) of the primary sensing circuitry 144.

At 408, the one or more processors utilize the ventricular features from the first CA data set to separate beat segments within the second CA data set. For example, R-waves and RR intervals within the CA signal may be tracked and used to separate the beat segments within the second CA data set.

At 410, the one or more processors automatically iteratively analyze the beat segments by (i) overlaying an atrial activity search window with the second data set, and (ii) determining whether one or more of the candidate atrial features occur within the atrial activity search window as described further below.

At 412, the one or more processors overlay an atrial activity search window with the second data set. For example, each ventricular feature (e.g., R-wave) identified in the first CA data set is used as a basis to define an atrial activity search window (e.g., 100-200 msec) preceding the ventricular feature. Additionally or alternatively, refractory and/or blanking periods based on the ventricular features may be overlaid with the second data set in order to suppress detection of candidate atrial features outside of the atrial activity search window. In one example (see FIG. 5B), refractory periods (e.g., timer blanking for 250 msec) after R-waves may be used to blank P-waves on the atrial sensing channel. Other blanking periods (e.g., segments of P-wave refractory of 50 msec blanking between T- and R-waves) can be added to avoid frequent P-wave detections.

At 414, the one or more processors determine whether one or more of the candidate atrial features occur within the atrial activity search window as described further below. In one or more embodiments, based on detecting and saving candidate P-wave features to the candidate P-wave list, the process determines whether one or more of the candidate P-wave features occur within the atrial activity search window.

At 416 and 418, the one or more processors adjust an atrial sensitivity profile based on whether the atrial activity search window includes the one or more of the candidate atrial features. At 416, based on determining that the atrial activity search window does include the one or more candidate atrial features at 414, the one or more processors adjusts the atrial sensitivity profile by raising a sensitivity level (and reducing the threshold) of the atrial sensitivity profile. At 418, based on determining that the atrial activity search window does not include the one or more candidate atrial features at 414, the one or more processors adjusts the atrial sensitivity profile by reducing the sensitivity level (and raising the threshold) of the atrial sensitivity profile. The atrial sensitivity profile may be raised or reduced in preprogrammed increments. As one nonlimiting example, the sensitivity level of the atrial sensitivity profile may be raised or reduced by pre-programmed 0.025 mV increments to mitigate under-sensing and/or oversensing. Additionally or alternatively, the atrial sensitivity profile may be raised or reduced as a function of the amplitude of the candidate atrial features. For example, based on P-wave amplitudes exceeding or falling under the current sensitivity level of the atrial sensitivity profile by a relatively large margin (e.g., greater than 5 pre-programmed increments), the sensitivity level of the atrial sensitivity profile may be raised or reduced in multiples of the pre-programmed increments (e.g., 2-5 pre-programmed increments) in order to converge on peak the median value of the candidate atrial features.

The process may automatically iteratively analyze the beat segments, at least in part, by maintaining an estimate of a peak median value of the candidate atrial features based on adjusting sensitivity level of the atrial sensitivity profile. In one or more embodiments, the process may maintain an estimate of a P-wave peak median. Additionally or alternatively, the process may maintain an estimate of a T-wave peak median. Additionally or alternatively, the process may automatically iteratively analyze the beat segments, at least in part, by maintaining an estimate of a combination of an R-wave peak median, as the ventricular features, and the P-wave peak median and/or the T-wave peak median.

At 420, the one or more processors detect atrial events based on the atrial sensitivity profile. The one or more processors detect atrial events utilizing the updated atrial sensitivity profile (e.g., the P-wave peak median, the T-wave peak median) and the recent ventricular features (e.g., R-waves) to feed into the secondary discriminators (e.g., Brady, asystole, tachycardia, PVC, etc.) and confirm arrythmia detection. Additionally or alternatively, the one or more processors determine the peak median of the atrial sensing signals.

Figure 5A:
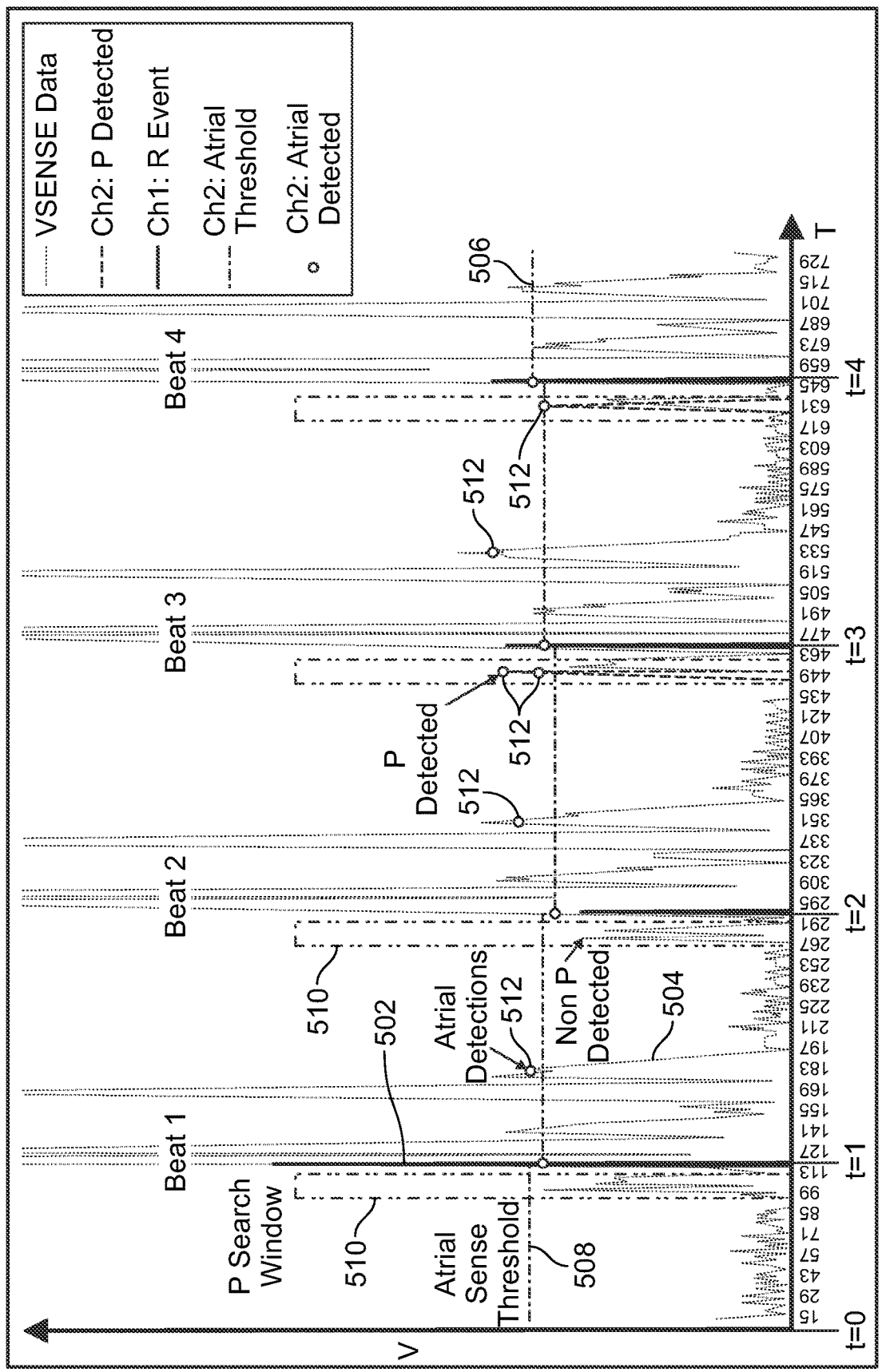
FIG. 5A illustrates an example of a timing diagram for CA signals analyzed by the atrial sensing process of FIG. 4 in accordance with embodiments herein.

FIG. 5A illustrates an example of a timing diagram for CA signals analyzed by the process of FIG. 4 in accordance with embodiments herein. The first CA data set 502 is obtained over the primary sensing channel and the second CA data set 504 is obtained over the secondary sensing channel. The sensitivity levels of the atrial sensitivity profile resulting from the process of FIG. 4 are indicated by the sensitivity level trend line 506. Prior to detecting the first ventricular feature at t=1 (e.g., upon start-up), the atrial sensitivity profile is set to an initial value 508 (e.g., 50% of the ventricular sensing threshold). Upon start up, the OAD process 136 obtains the first CA data set 502 over the primary sensing circuitry 144 and the second CA data set 504 over the secondary sensing circuitry 146. With reference to operation 404, the OAD process 136 detects candidate atrial features from the second CA data set 504 at points where the second CA signal crosses the atrial sensitivity profile. During the period from t=0 to t=1, the OAD process 136 does not detect any candidate atrial features. With reference to operation 406, the OAD process 136 identifies the first R-wave (Beat 1) in the first CA data set 502 at t=1. With reference to operations 408 and 410, the first R-wave is used to separate the first beat segment from the second beat segment (from t=1 to t=2) in the second CA data set 504 and to define an atrial activity search window 510 preceding the first R-wave. With reference to operation 412 and 414, the OAD process 136 overlays the atrial activity search window 510 on the second CA data set 504 prior to the first R-wave and determines whether one or more of the candidate atrial features (e.g., P-waves) occurred within the atrial activity search window 510. With reference to operation 418, the OAD process 136 determines that no candidate atrial features were detected within the atrial search window 510 and raises the sensitivity level of the atrial sensitivity profile by lowering the threshold. During the period from t=1 to t=2, the OAD process 136 detects one candidate atrial feature 512 based on the current sensitivity level of the atrial sensitivity profile. With reference to operation 406, the OAD process 136 identifies the second R-wave (Beat 2) in the first CA data set 502 at t=2. With reference to operations 408 and 410, the second R-wave is used to separate the second beat segment from the third beat segment (from t=2 to t=3) in the second CA data set 504 and to define the atrial activity search window 510 preceding the second R-wave. With reference to operation 412 and 414, the OAD process 136 overlays the atrial activity search window 510 on the second CA data set 504 prior to the second R-wave and determines whether one or more of the candidate atrial features (e.g., P-waves) occurred within the atrial activity search window 510. With reference to operation 418, the OAD process 136 determines again that no candidate atrial features were detected within the atrial search window 510 and raises the sensitivity level of the atrial sensitivity profile by lowering the threshold again. During the period from t=2 to t=3, the OAD process 136 repeats and detects one candidate atrial feature 512 within the atrial search window 510 based on the current sensitivity level of the atrial sensitivity profile. With reference to operation 416, the OAD process 136 determines that one or more candidate atrial features were detected within the atrial search window 510 and lowers the sensitivity level of the atrial sensitivity profile by raising the threshold. With reference to operation 420, the OAD process 136 converges on and tracks the P-wave peak median and R-wave peak amplitudes detected identified in the first CA data set 502 pursuant to calculating an under-sensing threshold used by an under-sensing asystole discriminator.

Figure 5B:
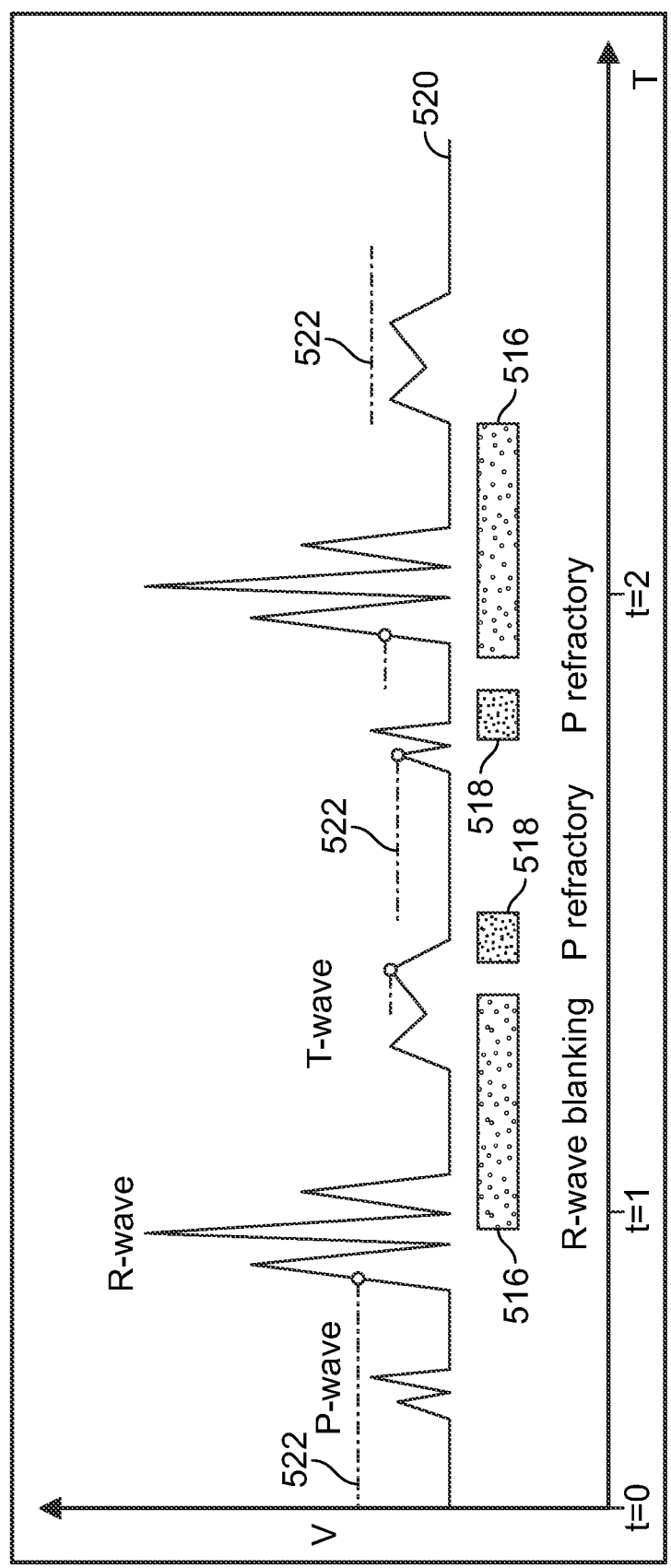
FIG. 5B illustrates an example of a timing diagram for CA signals analyzed by the ventricular and atrial sensing processes of FIG. 4 in accordance with embodiments herein.

FIG. 5B illustrates an example of a timing diagram for CA signals analyzed by the ventricular and atrial sensing process of FIG. 4 in accordance with embodiments herein. Additionally or alternatively to the example of 5A, the first R-wave and/or the second R-wave are used to define one or more blanking intervals 516 (e.g., the post-R-wave blanking window). The first CA data set is obtained over the primary sensing channel and the second CA data set is obtained over the secondary sensing channel. The CA waveform 520 illustrates the ventricular features (e.g., R waves) and atrial features (e.g., P-waves) detected by the OAD process 136 in the first and second data sets. The sensitivity levels of the atrial sensitivity profile resulting from the process of FIG. 4 are indicated by the sensitivity level trend line 522. In order to minimize the number of candidate atrial sensed events, one or more blanking intervals 516 may be used in addition to or as an alternative to the atrial activity search window 510 in FIG. 5A to narrow down the candidate P-wave list and optimize detection of P-waves. For example, a blanking interval 516 may be started with every ventricular sensed event (e.g., R-wave). In addition, one or more blanking intervals 518 may also be used to inhibit searching for candidate atrial sensed events. With reference to operation 412 and 414, the OAD process 136 overlays the atrial activity search window 510 and/or one or more blanking intervals 516 on the second CA data set and determines whether one or more of the candidate atrial features (e.g., P-waves) occurred within the atrial activity search window 510 and/or outside of the one or more blanking intervals 516 and 518. With reference to operation 418, the OAD process 136 determines that whether any candidate atrial features were detected within the atrial search window 510 and/or outside of the one or more blanking intervals 516 or 518 and adjusts sensitivity level of the atrial sensitivity profile as appropriate.

Figure 6:
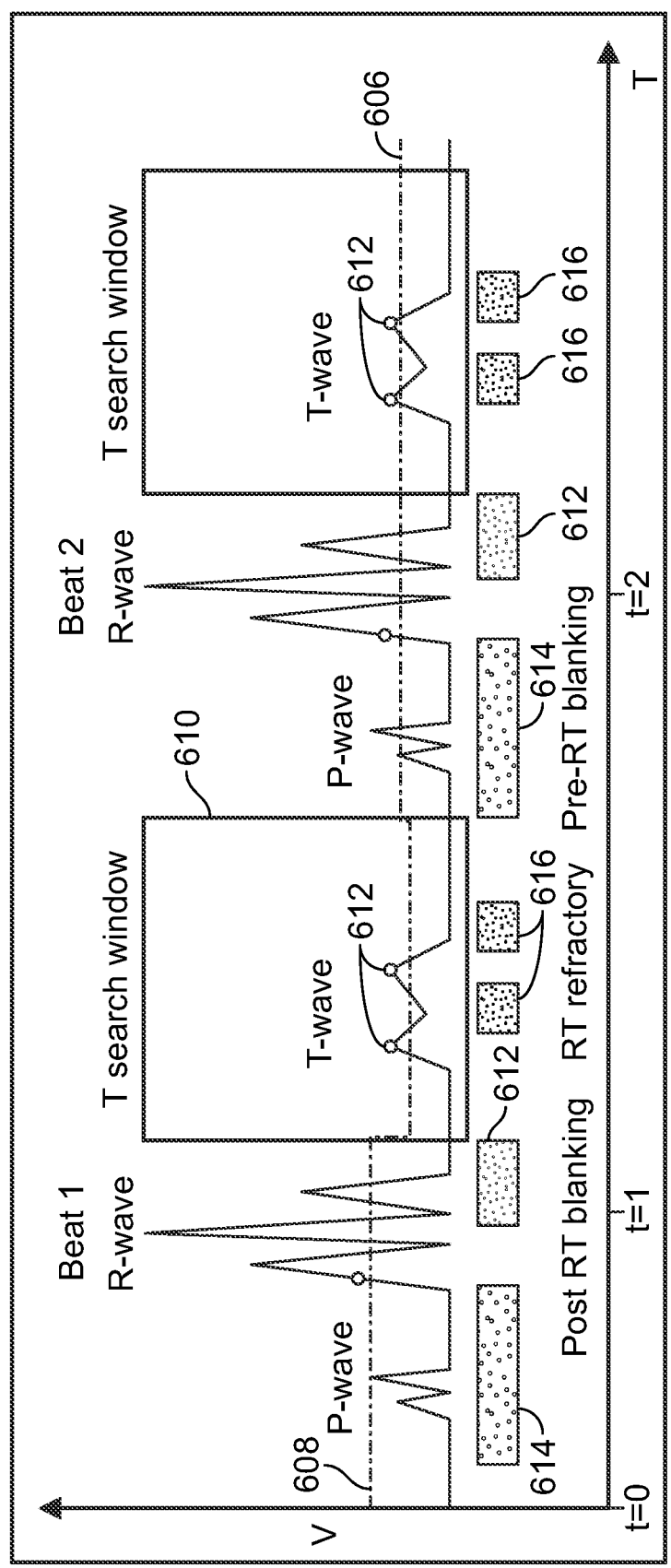
FIG. 6 illustrates a schematic example of CA signals analyzed by the process of FIG. 4 using blanking interval on the ventricular R-wave and T-wave sensing processes in accordance with embodiments herein.

FIG. 6 illustrates a schematic example of CA signals analyzed by the process of FIG. 4 using blanking interval on the ventricular R-wave and T-wave sensing processes in accordance with embodiments herein. The first CA data set is obtained over the primary sensing channel and the second CA data set is obtained over the secondary sensing channel. The CA waveform 602 illustrates the ventricular features (e.g., R waves) and separate ventricular relaxation features (e.g., T-waves) detected by the OAD process 136 in the first and second data sets. The sensitivity levels of the ventricular relaxation sensitivity profile resulting from the process of FIG. 4 are indicated by the sensitivity level trend line 606. Prior to detecting the first ventricular feature at t=1 (e.g., upon start-up), the ventricular relaxation sensitivity profile is set to an initial value 608 (e.g., 50% of the ventricular sensing threshold). Upon start up, the OAD process 136 obtains the first CA data set over the primary sensing circuitry 144 and the second CA data set over the secondary sensing circuitry 146. With reference to operation 404, the OAD process 136 detects candidate ventricular relaxation features from the second CA data set at points where the second CA signal crosses the ventricular relaxation sensitivity profile. During the period from t=0 to t=1, the OAD process 136 does not detect any candidate atrial features (e.g., P-waves). With reference to operation 406, the OAD process 136 identifies the first R-wave (Beat 1) in the first CA data set at t=1. With reference to operations 408 and 410, the first R-wave is used to separate the first beat segment from the second beat segment (from t=1 to t=2) in the second CA data set and to define an T search window 610 preceding the first R-wave (not shown). With reference to operation 412 and 414, the OAD process 136 overlays the T search window 610 on the second CA data set following the first R-wave and determines whether one or more of the candidate ventricular relaxation features (e.g., T-waves) occurred within the T search window 610. With reference to operation 418, the OAD process 136 determines that during the period from t=1 to t=2, the OAD process 136 detects two candidate ventricular relaxation features 612 based on the current sensitivity level of the ventricular relaxation sensitivity profile. With reference to operation 406, the OAD process 136 identifies the second R-wave (Beat 2) in the first CA data set at t=2. With reference to operations 408 and 410, the second R-wave is used to separate the second beat segment from subsequent beat segments in the second CA data set and to define the T search window 610 following the second R-wave. Additionally or alternatively, the first R-wave and/ or the second R-wave are used to define one or more blanking intervals (e.g., the post-R-wave blanking window 612, the pre-R-wave blanking window 614, R-T refractory intervals 161, and the like). The one or more blanking intervals 612, 614, 616 may be used to narrow down the candidate T-wave list and optimize detection of T-waves. With reference to operation 412 and 414, the OAD process 136 overlays the T search window 610 and one or more blanking intervals 612, 614, 616 on the second CA data set prior to the second R-wave and determines whether one or more of the candidate atrial features (e.g., T-waves) occurred within the T search window 610. With reference to operation 418, the OAD process 136 determines that two candidate atrial features 612 were detected within the atrial search window 610 and lowers the sensitivity level of the ventricular relaxation sensitivity profile by raising the threshold. With reference to operation 420, the OAD process 136 converges on and tracks the T-wave peak median and R-wave peak amplitudes detected identified in the first CA data set pursuant to feeding into secondary discriminators.

Figure 7A:
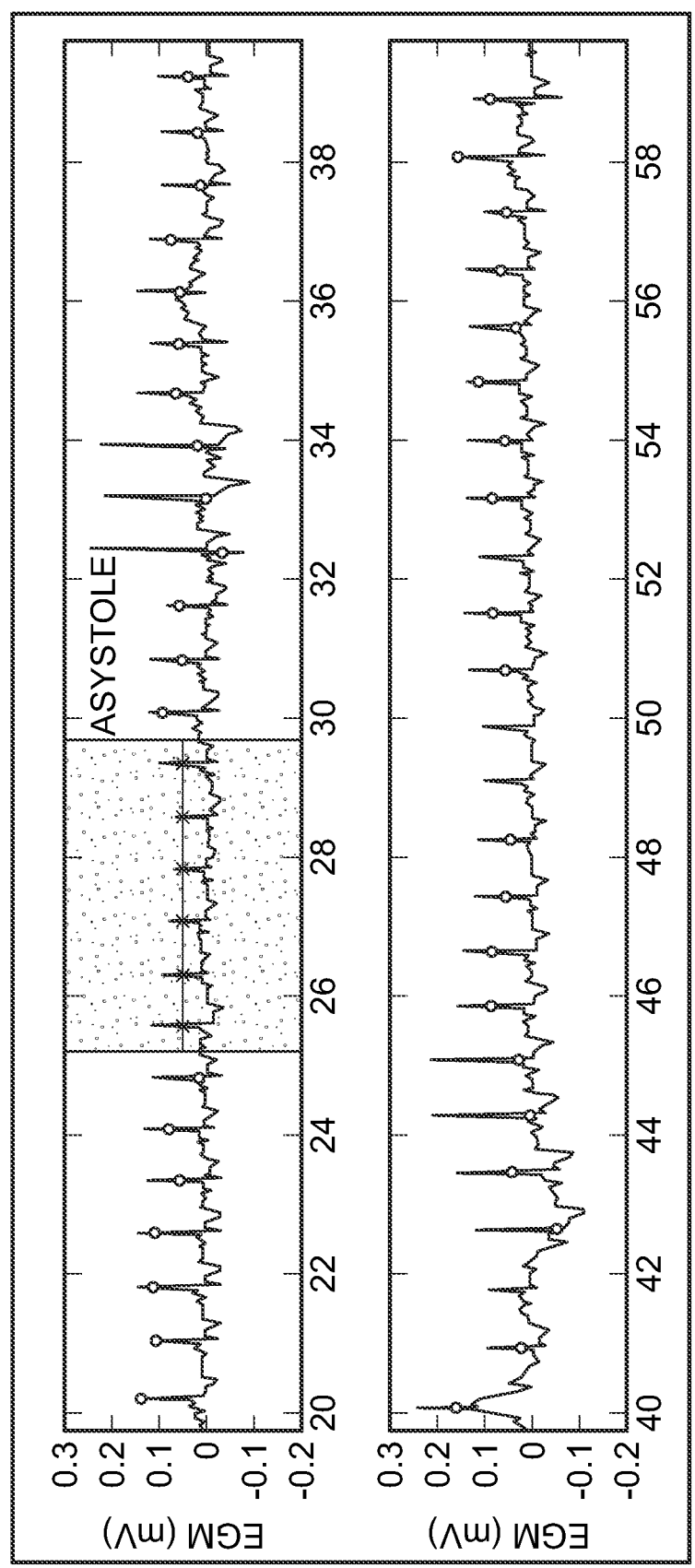
FIG. 7A illustrates timing diagrams for CA signals analyzed by the process of FIG. 4 in connection with an asystole under-sensing discriminator in accordance with embodiments herein.

FIG. 7A illustrates timing diagrams for CA signals analyzed by the process of FIG. 4 in connection with an asystole under-sensing discriminator in accordance with embodiments herein. When the asystole primary stage is triggered, instead of performing the full discriminator logic on the Pre-Trigger Analysis window (including baseline drift adjustment, searching for R-wave/P-wave peak values, sorting and finding medians), the under-sensing threshold is pre-determined during lightweight real-time operation on the P- and R-wave detection of two sensing channels. The flow would continue with the search for under-sensed beats in the asystole window (dot-shaded interval in FIG. 7A) which is estimated to exhibit significantly faster run-time compared to discriminators thereby achieving significant reduction of execution time of the discriminator, minimal marker delay and significant battery saving.

Figure 7B:
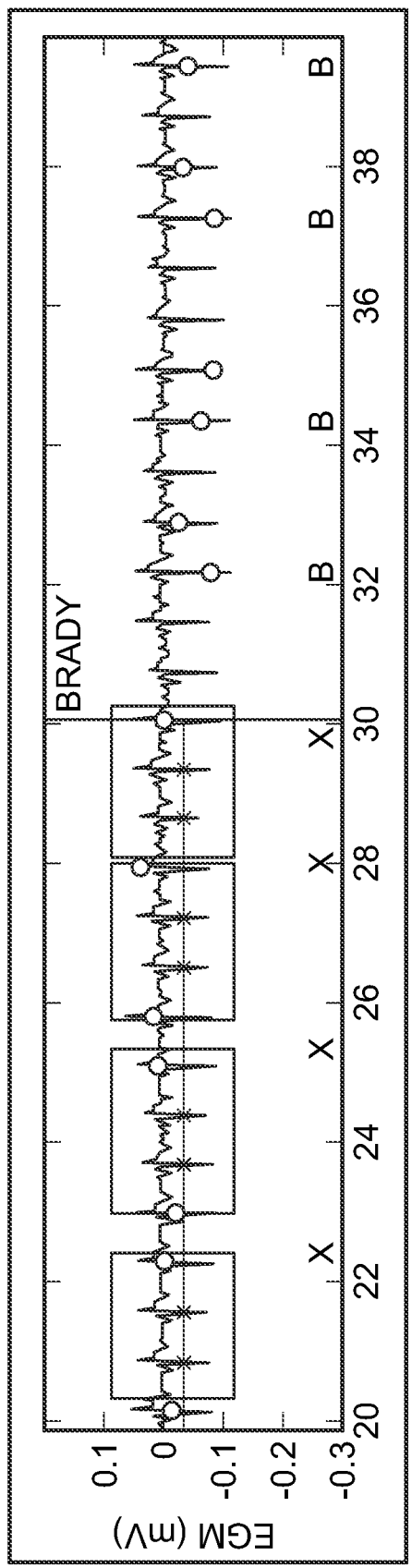
FIG. 7B illustrates a timing diagram for CA signals analyzed by the process of FIG. 4 in connection with a bradycardia under-sensing discriminator in accordance with embodiments herein.

FIG. 7B illustrates a timing diagram for CA signals analyzed by the process of FIG. 4 in connection with a bradycardia under-sensing discriminator in accordance with embodiments herein. Similar to the asystole under-sensing discriminator, when the bradycardia primary stage is triggered, the under-sensing threshold is readily available from lightweight real-time operation on the P- and R-wave detection of two sensing channels. The flow would continue with the search for under-sensed beats in the bradycardia windows (squared intervals in FIG. 7B) which exhibits significantly faster run time compared to a secondary discriminator thereby achieving significant reduction of execution time, minimal marker delay and significant battery saving.

Figure 8:
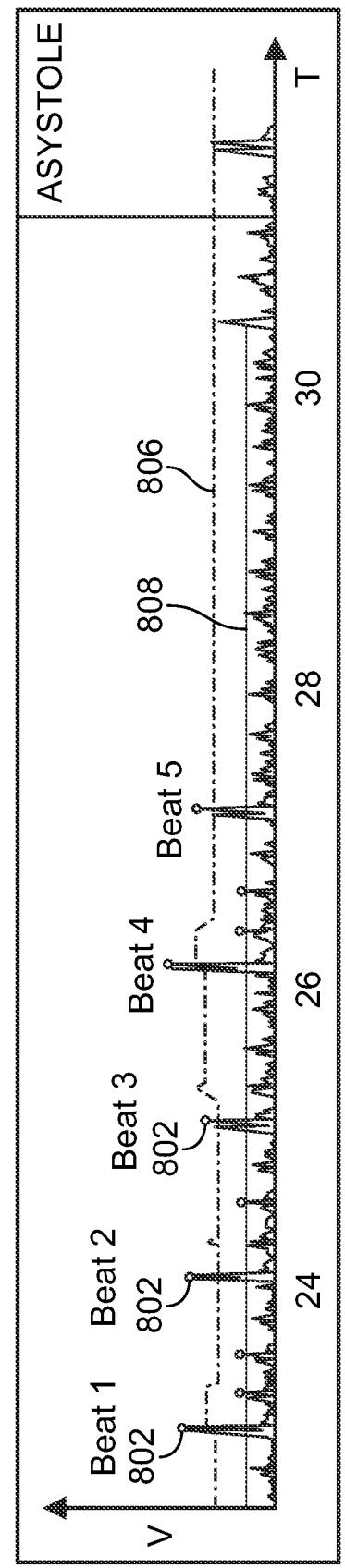
FIG. 8 illustrates a timing diagram for CA signals analyzed by the process of FIG. 4 in connection with adaptively adjusting the primary sensitivity profile in accordance with embodiments herein.

FIG. 8 illustrates a timing diagram for CA signals analyzed by the process of FIG. 4 in connection with adaptively adjusting the primary sensitivity profile in accordance with embodiments herein. The OAD process 136 may manage the primary (e.g., ventricular) sensitivity profile of the primary sensing circuit 144 by adjusting the sensitivity level of the ventricular sensitivity profile based on the current atrial sensitivity profile. The sensitivity level of the atrial sensitivity profile (indicated by trend line 808) and the separation of R-wave peaks 802 over the ventricular maximum sensing threshold (the horizontal portions of trend line 806) (e.g., the R-wave peak amplitude clearance) may be used on a beat-to-beat basis to dynamically adjust the sensitivity level of the ventricular sensitivity profile. The separation between R-wave peaks 802 and a minimum sensitivity level/maximum sensing threshold (indicated by trend line 806) for the ventricular sensitivity profile, and the real-time atrial sensitivity profile 808 may be used as an upper and lower bound, respectively, to dynamically adjust a maximum sensitivity level for the ventricular sensitivity profile. For example, based on the R-wave peak amplitude clearance being above a small value (e.g., 2 steps), the maximum sensitivity is not changed. Additionally or alternatively, based on the R-wave peak amplitude clearance being below a small value (e.g., 2 steps), then the maximum sensitivity is decreased (e.g., increasing sensitivity) only up to a safe clearance (e.g., 0.050 mV or 3 counts) from sensitivity level of the atrial sensitivity profile (indicated by trend line 808) in order to adapt sensing to changes in R-wave amplitude without causing P-wave over-sensing. The primary sensitivity profile parameters may be adjusted in accordance with embodiments herein, such as to achieve improved R-wave sensing without risking P-wave oversensing. Based on a pre-determined under-sensing threshold being calculated and adjusted on each ventricular sense event, adaptively adjusting the ventricular sensing profile may be useful in reducing under-sensing, especially in bradycardia events where sensitivity levels may result in near-misses of R-waves.

Closing

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random-access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A system for detecting arrhythmias in cardiac activity, comprising:
   memory configured to store specific executable instructions;
   one or more processors configured to execute the specific executable instructions for:
   obtaining first and second far field cardiac activity (CA) data sets over primary and secondary sensing channels, respectively, in connection with a series of beats;
   detecting candidate atrial features from the second CA data set;
   identifying ventricular features from the first CA data set;
   utilizing the ventricular features to separate beat segments within the second CA data set;
   automatically iteratively analyzing the beat segments by:
      overlaying an atrial activity search window with the second CA data set; and
      determining whether one or more of the candidate atrial features occur within the atrial activity search window;
      adjusting an atrial sensitivity profile based on whether the atrial activity search window includes the one or more of the candidate atrial features; and
      detecting atrial events based on the atrial sensitivity profile.

2. The system of claim 1, wherein the primary and secondary sensing channels correspond to ventricular and atrial sensing channels respectively, the one or more processors configured to identify peaks in the second CA data set as the candidate atrial features, the one or more processors configured to identify the ventricular features by identifying R-waves in the first CA data set.

3. The system of claim 1, wherein the adjusting further comprises reducing a sensitivity level of the sensitivity profile when the determining determines that the atrial activity search window does not include the one or more candidate atrial features.

4. The system of claim 1, wherein the adjusting further comprises raising a sensitivity level of the atrial sensitivity profile when the determining determines that the atrial activity search window does include the one or more candidate atrial features.

5. The system of claim 1, wherein the candidate atrial features includes detecting candidate P-wave features and saving the candidate P-wave features to a candidate P-wave list, the determining operation including determining whether one or more of the candidate P-wave features occur within the atrial activity search window.

6. The system of claim 1, wherein the candidate atrial features correspond to P-wave peaks and the automatically iteratively analyzing the beat segments maintains an estimate of a P-wave peak amplitude.

7. The system of claim 6, wherein ventricular features correspond to R-wave peaks and the automatically iteratively analyzing the beat segments maintains an estimate of a combination of an R-wave peak amplitude and the P-wave peak amplitude.

8. The system of claim 1, wherein the candidate atrial features correspond to T-wave peaks and the automatically iteratively analyzing the beat segments maintains an estimate of a T-wave peak amplitude.

9. The system of claim 8, wherein ventricular features correspond to R-wave peaks and the automatically iteratively analyzing the beat segments maintains an estimate of a combination of an R-wave peak amplitude and the T-wave peak amplitude.

10. The system of claim 1, further comprising adjusting a ventricular sensitivity profile based at least in part on the atrial sensitivity profile.

11. A method for detecting arrhythmias in cardiac activity, comprising:
    under control of one or more processors configured with specific executable instructions:
    obtaining first and second far field cardiac activity (CA) data sets over primary and secondary sensing channels, respectively, in connection with a series of beats;
    detecting candidate atrial features from the second CA data set;
    identifying ventricular features from the first CA data set;
    utilizing the ventricular features to separate beat segments within the second CA data set;
    automatically iteratively analyze the beat segments by:
       overlaying an atrial activity search window with the second CA data set; and
       determining whether one or more of the candidate atrial features occur within the atrial activity search window;
       adjusting an atrial sensitivity profile based on whether the atrial activity search window includes the one or more of the candidate atrial features; and
       detecting atrial events based on the atrial sensitivity profile.

12. The method of claim 11, wherein the primary and secondary sensing channels correspond to ventricular and atrial sensing channels respectively, wherein the method includes, as part of detecting candidate atrial features, identifying peaks in the second CA data set as the candidate atrial features, and wherein the method includes, as part of identifying ventricular features, identifying R-waves in the first CA data set.

13. The method of claim 11, wherein the method further comprises, as part of the adjusting, reducing a sensitivity level of the sensitivity profile when the determining determines that the atrial activity search window does not include the one or more candidate atrial features.

14. The method of claim 11, wherein the method further comprises, as part of the adjusting, raising a sensitivity level of the atrial sensitivity profile when the determining determines that the atrial activity search window does include the one or more candidate atrial features.

15. The method of claim 11, wherein the method further comprises: saving the candidate atrial features to a candidate atrial feature list, and, as part of the determining, determining whether one or more of the candidate atrial features occur within the atrial activity search window.

16. The method of claim 11, wherein the candidate atrial features correspond to P-wave peaks, and wherein the method includes, as part of the automatically iteratively analyzing the beat segments, maintaining an estimate of a P-wave peak amplitude.

17. The method of claim 16, wherein ventricular features correspond to R-wave peaks, and wherein the method includes, as part of the automatically iteratively analyzing the beat segments, maintaining an estimate of a combination of an R-wave peak amplitude and the P-wave peak amplitude.

18. The method of claim 11, wherein the candidate atrial features correspond to T-wave peaks, and wherein the method includes, as part of the automatically iteratively analyzing the beat segments, maintaining an estimate of a T-wave peak amplitude.

19. The method of claim 18, wherein ventricular features correspond to R-wave peaks, and wherein the method includes, as part of the automatically iteratively analyzing the beat segments, maintaining an estimate of a combination of an R-wave peak amplitude and the T-wave peak amplitude.

20. The method of claim 11, further comprising adjusting a ventricular sensitivity profile based at least in part on the atrial sensitivity profile.

* * * * *